United States Patent
Mohr et al.

(10) Patent No.: US 11,200,976 B2
(45) Date of Patent: Dec. 14, 2021

(54) TRACKING METHOD AND APPARATUS

(71) Applicant: Canon Medical Systems Corporation, Otawara (JP)

(72) Inventors: Brian Mohr, Edinburgh (GB); Ewan Hemingway, Edinburgh (GB); Paul Thomson, Edinburgh (GB); Georgios Diakidis, Edinburgh (GB)

(73) Assignee: Canon Medical Systems Corporation, Otawara (JP)

( * ) Notice: Subject to any disclaimer, the term of this patent is extended or adjusted under 35 U.S.C. 154(b) by 89 days.

(21) Appl. No.: 16/549,443

(22) Filed: Aug. 23, 2019

(65) Prior Publication Data
US 2021/0057081 A1 Feb. 25, 2021

(51) Int. Cl.
*G16H 30/00* (2018.01)
*G16H 30/40* (2018.01)
(Continued)

(52) U.S. Cl.
CPC ........... *G16H 30/40* (2018.01); *G06N 3/08* (2013.01); *G06T 7/0012* (2013.01); *G06T 7/12* (2017.01);
(Continued)

(58) Field of Classification Search
CPC .......... G16H 30/40; G16H 50/20; G06T 7/12; G06T 7/70; G06T 7/0012;
(Continued)

(56) References Cited

U.S. PATENT DOCUMENTS

| 7,043,290 B2 | 5/2006 | Young et al. |
|---|---|---|
| 8,731,271 B2 | 5/2014 | Rens et al. |

(Continued)

FOREIGN PATENT DOCUMENTS

| CN | 106504232 A | 3/2017 |
|---|---|---|
| CN | 107563983 A | 1/2018 |

(Continued)

OTHER PUBLICATIONS

Wolterink et al., "Coronary Artery Centerline Extraction in Cardiac CT Angiography Using a CNN-Based Orientation Classifier", Medical Image Analysis, vol. 51, Jan. 2019, pp. 46-60.
(Continued)

*Primary Examiner* — Khai M Nguyen
(74) *Attorney, Agent, or Firm* — Oblon, McClelland, Maier & Neustadt, L.L.P.

(57) ABSTRACT

A method of determining a path of a tubular structure comprises: obtaining volumetric medical imaging data that represents anatomy of a subject including the tubular structure; performing a position-determining procedure that comprises: obtaining an initial position of a current point on said path of the tubular structure; selecting a sub-region based on said initial position; obtaining values of at least one parameter representative of the tubular structure; inputting to a trained model both data from said selected sub-region and said parameter values, the trained model having been trained to determine paths of tubular structures; outputting by the trained model a position for a next point on said path of the tubular structure; and updating said initial position to said next point; and repeating the position-determining procedure for updating the initial position thereby to obtain the path of the tubular structure.

20 Claims, 6 Drawing Sheets

(51) Int. Cl.
*G06N 3/08* (2006.01)
*G16H 50/20* (2018.01)
*G06T 7/00* (2017.01)
*G06T 7/70* (2017.01)
*G06T 7/12* (2017.01)

(52) U.S. Cl.
CPC ............... *G06T 7/70* (2017.01); *G16H 50/20* (2018.01); *G06T 2207/20084* (2013.01); *G06T 2207/30004* (2013.01)

(58) Field of Classification Search
CPC G06T 2207/20084; G06T 2207/30004; G06N 3/08
See application file for complete search history.

(56) References Cited

U.S. PATENT DOCUMENTS

| | | |
|---|---|---|
| 9,767,557 B1 | 9/2017 | Gulsun et al. |
| 10,083,504 B2 | 9/2018 | Bronkalla et al. |
| 2014/0003701 A1* | 1/2014 | Masood ................ G06T 7/0012 382/134 |
| 2014/0355854 A1* | 12/2014 | Kelm ...................... G06T 7/149 382/131 |
| 2015/0065846 A1 | 3/2015 | Choi et al. |
| 2016/0110874 A1* | 4/2016 | Matthews ............. G06T 11/203 382/131 |
| 2016/0148371 A1* | 5/2016 | Itu ......................... A61B 8/065 382/128 |
| 2016/0155234 A1 | 6/2016 | Kang et al. |
| 2016/0180525 A1* | 6/2016 | Reynolds .............. G06T 7/0016 382/131 |
| 2017/0262733 A1 | 9/2017 | Gulsun et al. |
| 2018/0000441 A1 | 1/2018 | Wang et al. |
| 2018/0218514 A1 | 8/2018 | Berger et al. |
| 2018/0247414 A1* | 8/2018 | Novikov ................. G06T 7/143 |
| 2019/0172211 A1 | 6/2019 | Novikov et al. |
| 2019/0244363 A1* | 8/2019 | Tan ......................... G06T 15/08 |
| 2019/0318476 A1* | 10/2019 | Isgum .................. A61B 6/5217 |
| 2019/0362494 A1* | 11/2019 | Wang ................... G06K 9/6273 |

FOREIGN PATENT DOCUMENTS

| | | |
|---|---|---|
| CN | 108830848 A | 11/2018 |
| WO | WO 2017/047819 A1 | 3/2017 |
| WO | WO 2018/029237 A1 | 2/2018 |
| WO | WO 2018/166824 A1 | 9/2018 |

OTHER PUBLICATIONS

Han D, et al., "Automatic Coronary Artery Segmentation Using Active Search for Branches and Seemingly Disconnected Vessel Segments from Coronary CT Angiography." PLoS ONE 11 (8): e0156837. https://doi.org/10.1371/journal.pone.0156837, 2016, pp. 1-24.

Zhang, P, et al., "Deep Reinforcement Learning for Vessel Centerline Tracing in Multi-modality 3D Volumes," 21st International Conference, Granada, Spain, Sep. 16-20, 2018, Proceedings, Part IV. 10.1007/978-3-030-00937-3_86, 2018, pp. 755-763.

* cited by examiner

TRACKING METHOD AND APPARATUS

FIELD

Embodiments described herein relate generally to a tracking apparatus and method, for example an apparatus and method for tracking vessels, airways, or other tubular structures in medical imaging. Optionally, the apparatus and method may also perform segmentation.

BACKGROUND

It is known to use coronary vessel tracking and segmentation algorithms to track and segment coronary vessels in cardiac applications.

More generally, tubular tree structures (for example, vessels and airways) are common in anatomy and there are many uses for their segmentation. Many algorithms have been developed for tracking vessels and other tubular tree structures, and for segmenting vessels and other tubular tree structures.

Existing vessel tracking and/or segmentation methods may often require manual correction of tracking and/or segmentation results. It has been found that fully automated vessel centerline tracking (and segmentation) without the need for manual correction is a difficult task.

A common issue in vessel tracking is that an incorrect path may be taken when encountering a loop in the vessel, where the incorrect path shortcuts the loop. An example of such a shortcut is shown in FIG. 1.

FIG. 1 is a schematic illustration of a vessel 10 having a loop 12. A vessel tracking algorithm is initiated at a point 14 at the left of the illustration. The tracking of the vessel proceeds in steps of a given step size to subsequent points 16, 18, 20, 22, 24 which are located along the vessel. After step 24, a correct path would be to follow the loop by continuing the track in a generally upwards direction. However, the vessel tracking algorithm for which results are shown in FIG. 1 proceeds to points 26, 28 on the vessel beyond the loop. The loop is therefore omitted from the tracked version of the vessel.

BRIEF DESCRIPTION OF THE DRAWINGS

Embodiments are now described, by way of non-limiting example, and are illustrated in the following figures, in which.

DETAILED DESCRIPTION OF THE DRAWINGS

Figure 1:
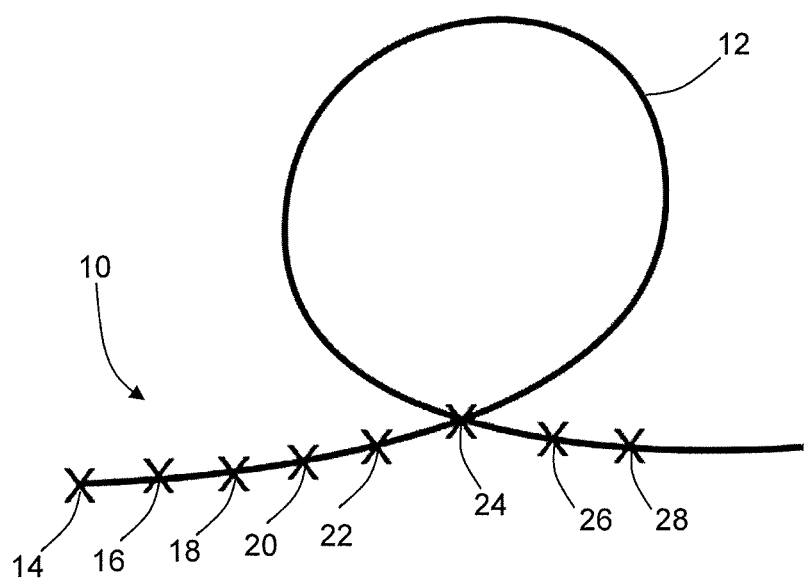
FIG. 1 is a schematic illustration of a known method of vessel tracking.

Certain embodiments provide a method of determining a path of a tubular structure, comprising: obtaining volumetric medical imaging data that represents anatomy of a subject including the tubular structure; performing a position-determining procedure that comprises: obtaining an initial position of a current point on said path of the tubular structure; selecting a sub-region based on said initial position; obtaining values of at least one parameter representative of the tubular structure; inputting to a trained model both data from said selected sub-region and said parameter values, the trained model having been trained to determine paths of tubular structures; outputting by the trained model a position for a next point on said path of the tubular structure; and updating said initial position to said next point; and repeating the position-determining procedure for updating the initial position thereby to obtain the path of the tubular structure.

Certain embodiments provide an apparatus comprising processing circuitry configured to perform a method for determining a path of a tubular structure, the method comprising: obtaining volumetric medical imaging data that represents anatomy of a subject including the tubular structure; performing a position-determining procedure that comprises: obtaining an initial position of a current point on said path of the tubular structure; selecting a sub-region based on said initial position; obtaining values of at least one parameter representative of the tubular structure; inputting to a trained model both data from said selected sub-region and said parameter values, the trained model having been trained to determine paths of tubular structures; outputting by the trained model a position for a next point on said path of the tubular structure; and updating said initial position to said next point; and repeating the position-determining procedure for updating the initial position thereby to obtain the path of the tubular structure.

Certain embodiments provide a method for training a model to determine paths of tubular structures, the method comprising: obtaining a plurality of training sets of volumetric medical imaging data, each representing anatomy of a respective subject including a respective tubular structure; obtaining a respective ground truth track for each of the training sets of volumetric medical imaging data; for each of the training sets of volumetric medical imaging data, obtaining data for a plurality of sub-regions along the respective tubular structure; and training the model to determining paths of tubular structures using data from sub-regions and values for at least one parameter representative of the tubular structure.

Certain embodiments provide an apparatus comprising processing circuitry configured to perform a method for training a model to determine paths of tubular structures, the method comprising: obtaining a plurality of training sets of volumetric medical imaging data, each representing anatomy of a respective subject including a respective tubular structure; obtaining a respective ground truth track for each of the training sets of volumetric medical imaging data; for each of the training sets of volumetric medical imaging data, obtaining data for a plurality of sub-regions along the respective tubular structure; and training the model to determining paths of tubular structures using data from sub-regions and values for at least one parameter representative of the tubular structure.

Figure 2:
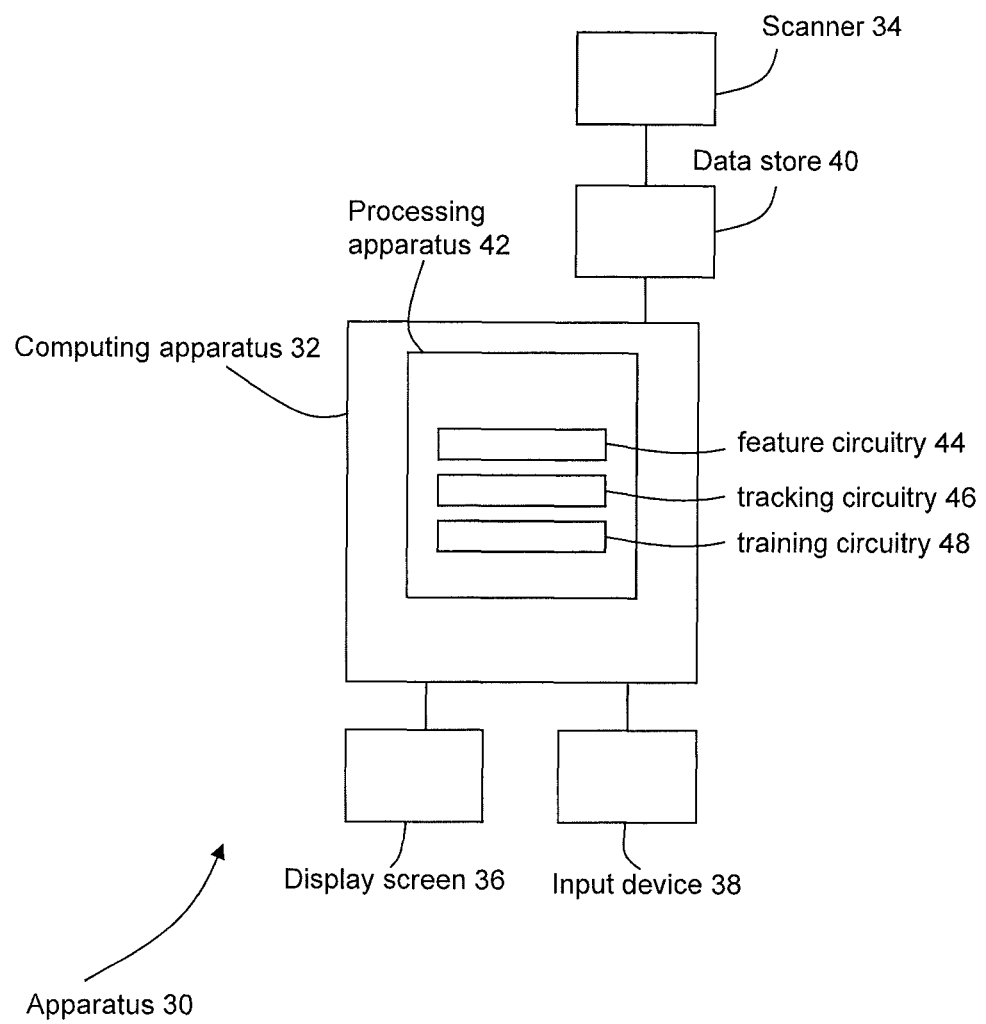
FIG. 2 is a schematic diagram of an apparatus according to an embodiment.

An image processing apparatus 30 according to an embodiment is illustrated schematically in FIG. 2.

The image processing apparatus 30 comprises a computing apparatus 32, in this case a personal computer (PC) or workstation, which is connected to a scanner 34 via a data store 40. In the embodiment of FIG. 2, the data store 40 is an image data server 40.

The image processing apparatus 30 further comprises one or more display screens 36 and an input device or devices 38, such as a computer keyboard, mouse or trackball.

In the present embodiment, the scanner 34 is a CT (computed tomography) scanner which is configured to obtain volumetric CT scans, for example coronary CTA scans. In other embodiments, the scanner 34 may be any scanner that is configured to perform medical imaging. The scanner 34 is configured to generate image data that is representative of at least one anatomical region of a patient or other subject. In the present embodiment, the anatomical region comprises the coronary arteries. In other embodiments, the at least one anatomical region may comprise any tubular anatomical structure, for example any vessel or airway.

The scanner 34 may be configured to obtain two-dimensional or three-dimensional image data in any imaging modality. For example, the scanner 34 may comprise a magnetic resonance (MR) scanner, CT (computed tomography) scanner, cone-beam CT scanner, X-ray scanner or ultrasound scanner.

In some embodiments, the scanner 34 is configured to obtain a sequence of two-dimensional or three-dimensional image data sets over time. A sequence of three-dimensional image data may be referred to as four-dimensional image data. The sequence of image data may comprise multi-phase three-dimensional image data. The sequence of image data may comprise any appropriate sequence of image data, for example image data that is representative of perfusion. The four-dimensional image data may comprise a plurality of frames. Each of the frames may be representative of a respective time and/or a respective phase of motion.

In the present embodiment, image data sets obtained by the scanner 34 are stored in image data server 40 and subsequently provided to computing apparatus 32. In use, the scanner 34 applies a scan to a patient and generates image data. The scanner 34 sends the image data to the image data server 40. The image data server 40 updates an image data list to include the image data.

The computing apparatus 32 launches an application for use by a user, for example a clinician. The user selects image data from the image data list stored on the image data server 40. The computing apparatus 32 sends a request to the image data server 40 for the selected image data. The image data server 40 sends the selected image data to the computing apparatus 42. The computing apparatus 32 is configured to apply image processing to the image data, then output a result to its display 36.

In an alternative embodiment, image data sets are supplied from a remote data store (not shown). The data store 40 or remote data store may comprise any suitable form of memory storage.

Computing apparatus 32 comprises a processing apparatus 42 for processing of data, including image data. The processing apparatus comprises a central processing unit (CPU) and Graphical Processing Unit (GPU).

The processing apparatus 42 provides a processing resource for automatically or semi-automatically processing image data sets.

The processing apparatus 42 includes feature circuitry 44 configured to determine features in a selected sub-region of an imaging data set; tracking circuitry 46 configured to determine positions along a tubular structure; and training circuitry 48 configured to train machine learning models for feature determining and tracking. In other embodiments, a first apparatus may be used to train the machine learning models and a second, different apparatus may use the trained models for feature determining and tracking. In other embodiments, any suitable apparatus or combination of apparatuses may be used.

In the present embodiment, the circuitries 44, 46, 48 are each implemented in the CPU and/or GPU by means of a computer program having computer-readable instructions that are executable to perform the method of the embodiment. In other embodiments, the various circuitries may be implemented as one or more ASICs (application specific integrated circuits) or FPGAs (field programmable gate arrays).

The computing apparatus 32 also includes a hard drive and other components of a PC including RAM, ROM, a data bus, an operating system including various device drivers, and hardware devices including a graphics card. Such components are not shown in FIG. 2 for clarity.

The image processing apparatus 10 is configured to perform vessel tracking using values for curvature and torsion.

Figure 3:
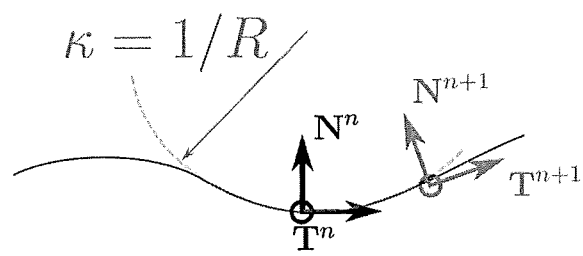
FIG. 3 is a schematic illustration representing curvature of an exemplary curve.

FIG. 3 is a schematic illustration representing curvature of an exemplary curve 80 in two dimensions. FIG. 3 shows a first point 82 (point $x_n$) and second point 84 (point $x_{n+1}$) on the curve 80. A step size between the first and second points may be written as $\Delta s$. At the first point 82, the tangent vector is $T^n$ and the normal vector is $N^n$. At the second point 84, the tangent vector is $T^{n+1}$ and the normal vector is $N^{n+1}$. The direction of the tangent and normal change as we move along the curve from the first point 82 to the second point 84. Intuitively, it may be considered that the tangent evolves to orientate towards the normal. It may be considered that the basis rotates following a circle of radius $$R = \frac{1}{\kappa}.$$

The curvature of the curve at point 82 may be given by $$\kappa = \frac{1}{R},$$

where R is the radius of the curve.

The basis vectors T and N evolve as follows:

$$\frac{dT}{ds} = \kappa N; \frac{dN}{ds} = -\kappa T$$

The evolution of the T and N vectors between point $x_n$ and point $x_{n+1}$ may be written as:

$$\frac{T^{n+1} - T^n}{\Delta s} = \kappa^n N^n; \frac{N^{n+1} - N^n}{\Delta s} = -\kappa^n T^n$$

$$T^{n+1} = T^n + \Delta s \kappa^n N^n; N^{n+1} = N^n - \Delta s \kappa^n T^n$$

This evolution strategy may be classed as an explicit Euler integrator. A next step is predicted only from information at the current time step. In other embodiments, different time stepping methods may be used. For example, time stepping methods may be used that use intermediate representations (for example, $\kappa^{n+1/2}$), which may be thought of as implicit or semi-implicit.

A position r(Δs) of the next point may be predicted by Taylor expansion to various orders, for example:

$$r(\Delta s) = r(0) + \Delta s T(0) + o(\Delta s)$$

$$r(\Delta s) = r(0) + \Delta s T(0) + \frac{\Delta s^2 \kappa(0)}{2} N(0) + o(\Delta s^2)$$

We turn to the three-dimensional case. To include out of plane motion, torsion τ is also considered. The torsion τ of a curve measures the extent to which the curve departs from the plane. A radius of torsion may be given by $$\sigma = \frac{1}{\tau}.$$

A third vector B is introduced, where B is the cross product of T and N as shown below. We note that the letter B may also be used to indicate the set of basis vectors T,N,B. For example, B is used to refer to the entire set of basis vectors in FIG. 6 and the associated description.

In three dimensions, the basis vectors evolve as follows:

$$\frac{dT}{ds} = \kappa N; \frac{dN}{ds} = -\kappa T + \tau B; \frac{dB}{ds} = -\tau N$$

To predict the next step, the expansion is at least third order in the step size. It also includes the derivative of the curvature, κ'.

$$r(\Delta s) = r(0) + \left(\Delta s - \frac{\Delta s^3 \kappa^2(0)}{6}\right) T(0) + \left(\frac{\Delta s^2 \kappa(0)}{2} + \frac{\Delta s^3 \kappa'(0)}{6}\right) N(0) + \left(\frac{\Delta s^3 \kappa(0) \tau(0)}{6}\right) B(0) + o(\Delta s^3)$$

An alternative approach is to assume constant curvature and torsion, and project the current path along a helix with those properties. Using an assumption of constant curvature and torsion may allow bigger steps to be taken than may be used in the case of a Taylor expansion.

Figure 4:
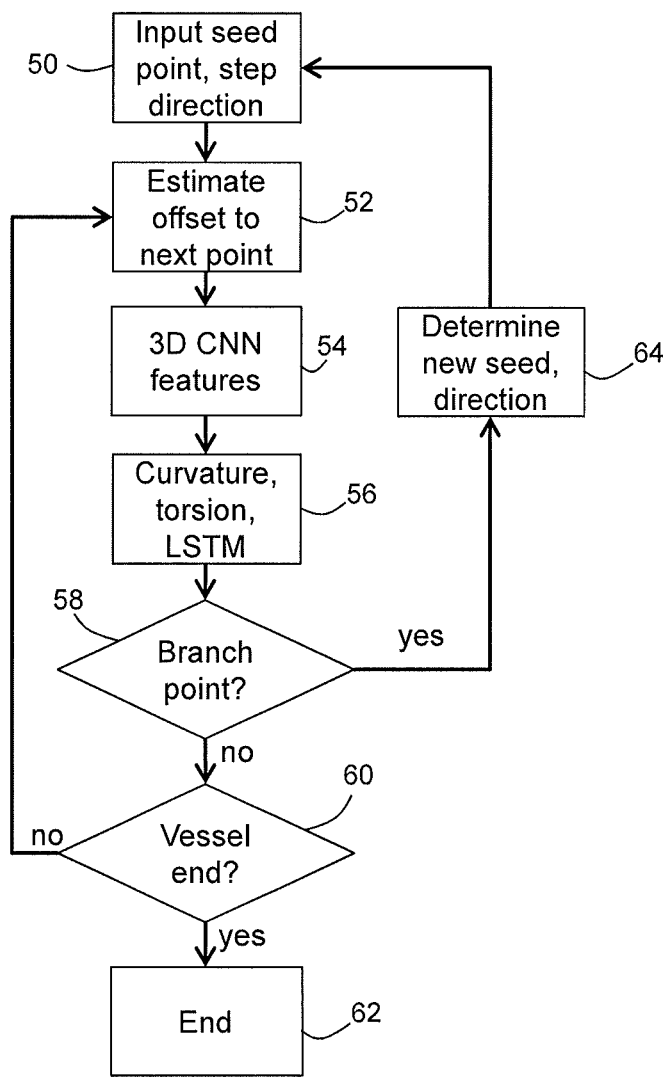
FIG. 4 is a flow chart illustrating in overview a method of an embodiment.

FIG. 4 is a flow chart illustrating in overview a vessel tracking method according to an embodiment. The image processing apparatus 30 of FIG. 2 is configured to perform a vessel tracking method as illustrated in FIG. 4.

The vessel tracking method of FIG. 4 comprises an iterative method which progresses through the vessel tree from a seed point by using deep learning. The evolution of the vessel is parameterized using torsion and curvature. At each point along a vessel, values for curvature and torsion are determined and are used to position a next point along the vessel. The steps between determined points along the vessel may be considered to be non-linear steps since they follow a curve determined by the curvature and torsion.

In some circumstances, the use of curvature and torsion in the vessel tracking instead of using linear steps along the vessel may result in more accurate tracking. In some circumstances, larger step sizes may be used than would be used with linear steps.

The vessel tracking method starts at stage 50 of FIG. 4. At stage 50, the feature circuitry 44 receives a volumetric medical imaging data set which is representative of a medical image of an anatomical region of a patient or other subject. In the present embodiment, the volumetric medical imaging data set comprises CT data. In other embodiments, the volumetric medical imaging data set may comprise data of any suitable modality.

In the present embodiment, the volumetric medical imaging data set is representative of the coronary region of a patient. In other embodiments, the volumetric medical imaging data set may be representative of any region having at least one tubular structure (for example, vessel or airway).

The feature circuitry 44 receives an input of a seed point for a vessel and an initial step direction. In the present embodiment, the seed point for the vessel and the initial step direction are provided by a user, for example a clinician. For example, the user may indicate a location for the seed point by clicking on an image that has been rendered from the volumetric medical imaging data set and displayed to the user. The user may indicate an initial direction of the vessel from the vessel seed point by positioning an arrow on the rendered image. In other embodiments, a user may use any suitable method for indicating a seed point and initial step direction. In further embodiments, the seed point and/or initial step direction may be determined automatically by the feature circuitry 44, or may be obtained using any suitable method.

A position-determining procedure is then performed by the feature circuitry 44 and tracking circuitry 46 to determine a next point on the vessel. The position-determining procedure comprises stages 52, 54 and 56 as described below.

At stage 52, the feature circuitry 44 estimates an offset from the seed point to a next point on the vessel. In the first iteration of stage 52, the estimated offset to the next point is found by taking a step of an initial step size in the initial step direction. The initial step size may be provided by the feature circuitry 44 as a default value, input by the user, or obtained using any other suitable method.

The feature circuitry 44 estimates a position of the next point on the vessel by adjusting the position of the seed point by the estimated offset.

At stage 54, the feature circuitry 44 determines a location of a sub-region in the coordinate space of the volumetric medical imaging data set. In the present embodiment, the sub-region is a cuboid which is centered on a position that is halfway between the position of the current point (which in the first iteration is the seed point) and the estimated position of the next point as determined at stage 52. The cuboid includes the current point and the estimated position of the next point. In the present embodiment, the sub-region is three-dimensional and may also be referred to as a sub-volume. In other embodiments, the sub-region may be two-dimensional or three-dimensional. Any suitable shape of sub-region may be used.

The size of the sub-region may be dependent on the step size between the current point and the estimated position of the next point. The size of the sub-region may be selected to include an entire estimated volume of the vessel between the current point and the estimated position of the next point. Optionally, the size of the sub-region may also be selected to include some surrounding tissue. An amount of surrounding tissue to be included may be predetermined. In other embodiments, the sub-region may be a subset of the estimated volume of the vessel between the current point and the estimated position of the next point. In some embodiments, the sub-region may be a two-dimensional slice of the estimated volume of the vessel. In other embodiments, the sub-region may be any suitable three-dimensional or two-dimensional region or regions. The sub-region may comprise a plurality of 2D slices. For example, the sub-region may comprise 2D slices on three orthogonal planes.

The feature circuitry 44 uses a first trained model to compute data from the selected sub-region. In the present embodiment, the first trained model is stored in data store 40. In other embodiments, the first trained model may be stored in any suitable memory, which may be local or remote. In other embodiments, the first trained model may be implemented in hardware, for example by using at least one ASIC or FPGA.

In the present embodiment, the first trained model is a convolutional neural network (CNN). The input to the first trained model comprises imaging data for the selected sub-region. For example, the imaging data for the selected sub-region may comprise respective intensity values for a plurality of voxels in the selected sub-region. In other embodiments, any suitable data associated with the selected sub-region may be used.

The output of the CNN comprises a convolution of the data for the selected sub-region. The output of the CNN is a vector of values for a plurality of features, where the features have emerged from the training of the CNN.

At stage 56, the feature circuitry 44 passes the vector of feature values that has been output from the CNN to the tracking circuitry 46.

The tracking circuitry 46 also receives values for a plurality of vessel parameters. In the present embodiment, the vessel parameters comprise curvature, torsion, step size, and vessel radius. In the initial iteration of stage 56, initial values for curvature, torsion, step size and vessel radius may be received by the tracking circuitry 46 when starting at the seed point. For example, curvature and torsion may initially be set to zero, and vessel radius and step size may be set to default values.

The tracking circuitry 46 inputs the vector of feature values from stage 54 and the values for the vessel parameters into a second trained model. In the present embodiment, the second trained model comprises a long short-term memory (LSTM). The second trained model is stored in data store 40. In other embodiments, the second trained model may be stored in any suitable memory, which may be local or remote. In other embodiments, the second trained model may be implemented in hardware, for example by using at least one ASIC or FPGA.

The second trained model processes the vector of feature values and the current values for the curvature, torsion, step size and radius. The second trained model outputs updated values for the curvature, torsion, step size and radius.

The tracking circuitry 46 uses the updated values for the curvature, torsion and step size to provide a position for the next point on the vessel. It is noted that an estimated position for this next point was previously provided at stage 52. The estimated position is superseded by the position determined at stage 56.

The centerline point position and basis using torsion, curvature and step size may be evolved by performing a Taylor expansion as described above with reference to FIG. 3. The centerline point position and basis using torsion, curvature and step size may be evolved assuming small deviations from constant values.

In the present embodiment, the second trained model comprises a long short-term memory (LSTM). In other embodiments, any suitable deep learning or machine learning model may be used, for example any suitable recurrent network. The recurrent network may be capable of determining how many past steps along the vessel to use to estimate each future step. In further embodiments, a model may be used that does not comprise a recurrent network. In such embodiments, a fixed number of steps may be used to predict a next step.

At stage 58, second trained model determines whether a branch point of the vessel has been reached. In the present embodiment, the second trained model performs a determination of whether the branch point has been reached concurrently with the determining of updated curvature, torsion, step size and radius values. The parameters that are regressed by the second trained model include a parameter indicating whether a branch point has been reached. In other embodiments, any suitable method may be used to determine whether a branch point has been reached.

If the answer at stage 58 is no, the tracking circuitry 46 proceeds to stage 60. If the answer is yes, the tracking circuitry 46 proceeds to stage 64.

We consider the case in which the answer to the branch point determination at stage 58 is no. The tracking circuitry 46 proceeds to stage 60.

At stage 60, the second trained model determines whether an end of the vessel has been reached. In the present embodiment, the second trained model performs a determination of whether an end of the vessel has been reached concurrently with the determining of curvature, torsion, step size and radius values. The parameters that are regressed by the second trained model include a parameter indicating whether an end of the vessel has been reached. In other embodiments, any suitable method may be used to determine whether an end of the vessel has been reached.

If the answer to stage 60 is yes, the tracking circuitry 46 proceeds to stage 62. If the answer is no, the tracking circuitry 46 starts another iteration of the position-determining procedure of stages 52 to 56.

The position-determining procedure may be repeated many times until an end of the vessel has been reached.

We consider a further iteration of the position-determining procedure. The further iteration described below may be any iteration along the length of the vessel that is not the initial iteration described above. The further iteration is described with reference to FIG. 5, which is a schematic illustration of an estimated next point $x_{n+1}$ and sub-region $\Omega$.

Figure 5:
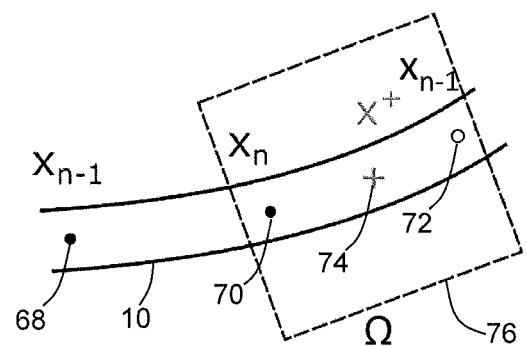
FIG. 5 is a schematic illustration of an estimated next point and sub-region.

FIG. 5 shows a determined position 70 of a current point $x_n$ on the vessel 10. The current point $x_n$ may be considered to be the nth point along the vessel 10. FIG. 4 also shows a determined position 68 of a preceding point $x_{n-1}$ on the vessel 10. The positions 68, 70 of the current point $x_n$ and preceding point $x_{n-1}$ have already been determined in previous iterations of the position-determining procedure.

Values of torsion $\tau_n$, curvature $\kappa_n$ step size $\Delta s_n$ and radius $R_n$ for the point $x_n$ are already known from a previous iteration of the position-determining procedure. A set of basis vectors $(B_n, x_n)$ for the point $x_n$ is also known.

At stage 52, the feature circuitry 44 estimates an offset to the next point. The estimated offset may be based on torsion $\tau_n$, curvature $\kappa_n$ and step size $\Delta s_n$ at point $x_n$. In other embodiments, any suitable method of estimating the offset may be used.

The feature circuitry 44 adjusts the position of point $x_n$ according to the estimated offset to obtain an estimated position 72 for a next point $x_{n+1}$ on the vessel. For example, the feature circuitry 44 may determine a path of a curved line portion having torsion $\tau_n$, curvature $\kappa_n$ and step size $\Delta s_n x_n$. The estimated position 72 of the next point $x_{n+1}$ may be at the end of the curved line portion determined by the feature circuitry 44. We note that the estimated position 72 for the next point will later be refined.

The feature circuitry 44 determines a position 74 of a point $x_+$ that is between the position 70 of the current point $x_n$, and the estimated position 72 of the next point $x_{n+1}$ along the vessel. In the present embodiment, the point $x_+$ is positioned halfway between the position 70 of the current point $x_n$, and the estimated position 72 of the next point along the vessel. The position 74 may be halfway along the curved line portion that joins the position 70 of the current point $x_n$ and the estimated position 72 of the next point $x_{n+1}$.

The position of the intermediate point $x_+$ is determined using an extrapolation function $f$. In the present embodiment, half of the step size is used so that the intermediate point $x_+$ is placed halfway between $x_n$ and the estimated position of $x_{n+1}$. In other embodiments, any fraction of the step size may be used. The set of basis vectors B is extrapolated using extrapolation function $f$ as follows:

$$(B_+, x_+) = f(\tau_n, \kappa_n, \frac{1}{2}\Delta s_n, B_n, x_n).$$

The feature circuitry 44 determines a position and extent of a cuboidal sub-region $\Omega$ (denoted as 76 in FIG. 5) that is centered on the halfway point $x_+$ and includes the position 70 of the current point $x_n$ and the estimated position 72 of the next point $x_{n+1}$. In other embodiments, any suitable shape and placement of sub-region 76 may be used.

At stage 54, the feature circuitry 44 uses the first trained model to obtain data from the sub-region 76. In the present embodiment, the data output by the feature circuitry 44 is a 3D convolution of image data for the sub-region 76. The data output by the feature circuitry 44 comprises a vector of feature values, where the features have been determined by the CNN. The data comprises features as described above. The feature circuitry 44 passes the determined features to the tracking circuitry 46.

At stage 56, the tracking circuitry 46 inputs the convolution from stage 54 into the second trained model. The tracking circuitry 46 also inputs into the second trained model a set of parameter values including values for torsion, curvature, step size and vessel radius.

Figure 6:
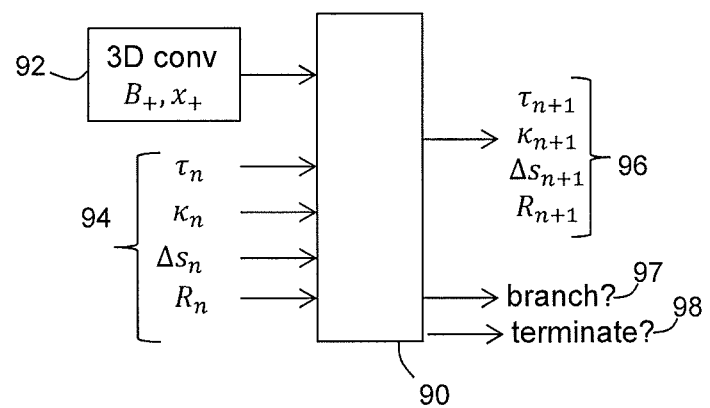
FIG. 6 is a schematic illustration of inputs and outputs to a trained model.

FIG. 6 is a schematic diagram showing inputs and outputs to the second trained model 90.

The second trained model receives input 92 comprising a vector 92 that is a 3D convolution of a sub-region $\Omega$ centered on the halfway point $x_+$.

Input 92 also includes a sets of basis vectors B.

The second trained model also receives values for parameters 94 including torsion $\tau_n$, curvature $\kappa_n$ step size $\Delta s_n$ and radius $R_n$ at point $x_n$. In other embodiments, the parameters 94 may include any suitable parameters that are representative of at least part of the vessel or other tubular structure.

CNN features 92 and previous step parameters 94 are input into the second trained model, which in the present embodiment is an LSTM 90. The LSTM 90 regresses the next step parameters. The LSTM 90 generates a set of outputs 96 comprising a new values for torsion $\tau_{n+1}$, curvature $\kappa_{n+1}$, step size $\Delta s_{n+1}$ and radius $R_{n+1}$. In other embodiments, any suitable parameters may be input and output.

Although only parameter values for the previous step are shown in FIG. 5, in embodiments the set of parameter values 84 that is input to the second trained model may include values for those parameters for some or all of the preceding points along the vessel. During training of the second trained model (described below), the second trained model may learn how many preceding points to take into account when predicting new values for the parameters. A recurrent network, for example an LSTM, may be able to take results for a variable number of preceding steps into account when predicting a next step. In some cases, a narrow window of steps may be used. In some cases, the full length of vessel segments (to the start of the vessel or to a branch point) may be used. In other embodiments, a fixed number of steps may be used.

The tracking circuitry 46 uses the output torsion $\tau_n$, curvature $\kappa_n$ and step size $\Delta s_n$ to determine an updated position (not shown in FIG. 4) for the next point. The updated position may be more accurate than the estimated position 72.

$$(B_{n+1}, x_{n+1}) = f(\tau_{n+1}, \kappa_{n+1}, \Delta s_{n+1}, B_n, x_n)$$

The position-determining procedure is repeated until a branch point or vessel end is reached. At each point along the vessel, features and step parameters including torsion and curvature are input into the second trained model (which in this embodiment is an LSTM) to regress the parameters to arrive at the next vessel centerline point. Iteration step size is also a regressed parameter. Iteration step size may be smaller where there are rapid changes to torsion or curvature than when torsion or curvature is changing slowly. Iteration step size may be smaller for points that are at or near a branch. Iteration step size may be larger for points that are not at or near a branch.

The LSTM 90 also outputs a determination 97 of whether a branch point has been reached. If the determination 97 indicates that a branch point has been reached, the LSTM 90 may output a predicted number of branches. The LSTM 90 also outputs a determination 98 of whether a vessel termination has been reached.

We turn to the case of a vessel end. In the present embodiment, the second trained model is trained to predict the end of the vessel. At each iteration of the position-determining procedure, the tracking circuitry 46 outputs a value for a parameter 98 that is indicative of whether the end of the vessel has been reached. At the end of a vessel, stage 60 returns a determination that the vessel has ended, and the process of FIG. 4 progresses to stage 62 at which the process ceases.

In the present embodiment, the LSTM 90 is trained to predict the end of the vessel based on the parameter values that are input to the second trained model. The LSTM 90 is trained to distinguish between a vessel ending and a blockage or partial blockage in the vessel, for example a soft plaque stenosis. In some circumstances, the imaging features and/or the history of the steps may suggest that a present position is not likely to be the end of the vessel.

In other embodiments, the second trained model may use any suitable method to predict the end of the vessel. In further embodiments, the end of the vessel may be predicted by the tracking circuitry 46 without the use of the second trained model. For example, the end of the vessel may be predicted by an analysis of a trend in vessel radius. A vessel end may be classified when the estimated radius decreases over a plurality of points in a consistent fashion. In some circumstances, a decrease in radius may be more sudden in the case of a blockage than in the case of the vessel terminating.

We turn now to a case in which the second trained model predicts a branch point at stage 58. In an iteration at a step near a branch point, the LSTM 90 regresses the number of branches at the branch point. In other embodiments, any suitable method may be used to predict a branch point and/or a number of branches. In some embodiments, the first trained model may be used to predict a branch point and/or a number of branches. In other embodiments, any suitable method may be used, which may or may not comprise a machine learning method.

For each branch, the tracking circuitry 46 proceeds to stage 64. At stage 64, the tracking circuitry 46 determines a new seed point for the branch and an initial direction for the branch. The initial direction may be based at least partially on information from the tracking of previous points. In some embodiments, a further trained model may be used to determine a seed point and/or an initial direction of tracking for the branch. The further trained model may be a further CNN, or set of CNNs. The CNN may be used in a region around the vessel to identify vessel features from which candidate branches may be determined. Branches may be selected from the candidate branches in accordance with the number of predicted branches. Branches may be selected in accordance with any appropriate metric. In other embodiments, the further trained model may be any suitable model. The further trained model may calculate any suitable features, for example hessian or gradients.

The flow chart of FIG. 4 returns to stage 50, at which the feature circuitry 44 receives the seed point and initial direction. The position-determining procedure of stages 52 to 56 is performed repeatedly to track the path of the branch as described above.

Each of the branches is tracked until an end of each branch is reached and the process of FIG. 4 ceases.

The tracking circuitry 46 outputs a set of tracked points that are representative of the path of the vessel, including any branches. The tracking circuitry 46 may output the set of tracked points to circuitry that is configured to perform a further process, for example coronary vessel analysis.

In some embodiments, a continuous or interpolated centerline is also generated in the method of FIG. 4. For example, torsion and curvature values may be used to draw a curve. Torsion and curvature values may be used to interpolate between tracked points to obtain a continuous curved line representing the centerline. In other embodiments, any suitable method may be used to obtain the centerline.

In further embodiments, the vessel is also segmented in the method of FIG. 4. For example, the first trained model may be trained to perform a segmentation a part of the vessel within the sub-region to which it is applied. The 3D CNN may be configured to perform fully convolutional segmentation of the structure. The 3D CNN may contain separate or additional layers to perform fully convolutional segmentation of the structure. The parts of the vessel that are segmented by the first trained model may then be combined to obtain a segmentation of the whole vessel. A fully segmented structure may be determined by a union of parts. In other embodiments, any suitable segmentation method may be used.

The method of FIG. 4 provides an iterative, 3D, recurrent deep learning approach to tubular tree structure tracking. Evolution is parameterized using torsion and curvature and includes features from a 3D convolution that is offset between the current step and a predicted next step.

A deep learning method is provided which may be trained with an achievable amount of data and annotation. The method may achieve sub-voxel accuracy in tracking.

The method may provide fully automated results without the use of manual correction. The fully automated results may act as an input to a further algorithm, for example an algorithm for performing coronary vessel analysis.

Torsion and curvature are used to provide tracking. Torsion and curvature are used to provide a predictive function in tracking, instead of merely being used as a constraint on a resulting shape. The use of torsion and curvature may allow non-linear steps to be taken along the vessel. A step may be provided that is curved in three dimensions. The use of torsion and curvature may provide a better fit to the vessel than would be provided by taking linear steps. In some circumstances, the use of torsion and curvature may allow larger steps to be taken along the vessel during the tracking process than would be possible if using linear steps. Torsion and curvature may provide a more natural parameterization of the path of a vessel, since vessels may generally be expected to have paths that curve in three dimensions.

In embodiments described above, the method of FIG. 4 is used to track a vessel. In other embodiments, the method of FIG. 4 may be used to track any suitable tubular structure, for example an airway.

In embodiments described above, the imaging data that is input to the method of FIG. 4 at stage 50 is three-dimensional (volumetric) imaging data. In other embodiments, the imaging data that is input to the method of FIG. 4 may comprise two-dimensional or four-dimensional imaging data.

We consider an embodiment in which the input comprises two-dimensional image data. The feature circuitry 44 receives the two-dimensional image data and processes the two-dimensional imaging data to obtain volumetric image data. For example, the feature circuitry 44 may combine multiple 2D slices to obtain an image volume. The feature circuitry 44 may perform an interpolation process. The resulting volumetric data is processed as described above with reference to FIG. 4.

We consider an embodiment in which the input comprises four-dimensional image data. The four-dimensional image data may comprise a plurality of three-dimensional data sets acquired over time. Each set of three-dimensional image data may correspond to a respective frame. The feature circuitry 44 is configured to obtain three-dimensional image data from the four-dimensional image data.

In one embodiment, a user selects a time frame of the four-dimensional image data. The feature circuitry 44 extracts three-dimensional image data corresponding to the selected time frame from the four-dimensional data. The resulting volumetric data is processed as described above with reference to FIG. 4.

In another embodiment, a user pre-defines a target time frame. The user may select a time frame based on a phase of motion. For example, the user may specify an end-diastole or end-systole frame. The feature circuitry 44 extracts three-dimensional imaging data from the four-dimensional imaging data automatically, based on the user's selected time frame. The resulting volumetric data is processed as described above with reference to FIG. 4.

We turn now to the training of the first trained model and second trained model that are used in the method of FIG. 4. Although we describe them as separate models, in other embodiments a single model may perform the functionality of the first trained model and second trained model as described above. In other embodiments, more trained models may be used. For example, multiple trained models may be applied to a given sub-region and/or a given vessel.

In the present embodiment, the training circuitry 48 receives a plurality of training data sets. Each training data set comprises a set of volumetric medical imaging data that is representative of a respective tubular structure. In the present embodiment, the training data sets comprise CT data. In other embodiments, training data sets of any suitable modality may be used. In some embodiments, domain adaptation techniques may be used to convert data sets acquired with one modality into data sets that appear to have been acquired with a different modality.

In the present embodiment, some of the training data sets are representative of vessels, and others of the training data sets are representative of airways. By training the models on both vessels and airways, a bigger training set may be provided. In other embodiments, the training data sets may be representative of a single type of tubular structure. In further embodiments, the training data sets may be representative of any suitable type or types of tubular structure. A domain adaptation technique may be used to adapt data sets that are representative of one type of tubular structure so that they look like data sets that are representative of a different type of tubular structure.

Vessels and other tubular structures may be of very diverse sizes. For example, vessels in different anatomical regions may have different sizes. A given vessel may branch into successively smaller vessels. A given vessel (for example a coronary artery) may be of different sizes in different individuals. It may also be the case that the size of vessels differs from the size of airways.

In some embodiments, the training data sets are scaled such that the vessels and airways of similar size in all of the training data sets. The sampling of the data may be dynamically scaled to a consistent, pre-determined value. Radius estimates from initial steps may be used to scale the data. The scaling may be used to provide a scale invariance in the training data.

In other embodiments, the trained models are trained on tubular structures of a diverse range of sizes. In such embodiments, each of the training data sets may be scaled to multiple sizes to provide additional training data. Training data may be scaled to several pixel resolutions. The scaling may be again considered to provide a scale invariance in the training data.

The training data sets are annotated with a ground truth vessel centerline. The training data sets may also be annotated with a ground truth segmentation. For example, the vessel segmentation may be represented by a contour (connected polyline) that is on a 2D plane that intersects (tangent to) the centerline. Successive planes taken at small steps may be combined to a 3D segmentation. Clinicians may manually adjust the points of the contour to define the segmentation ground truth. To obtain a centerline ground truth, a clinician may adjust the position of a centerline point, for example in a MPR (multiplanar reconstruction) or in a cross-cut (tangent to centerline) view.

Figure 7:
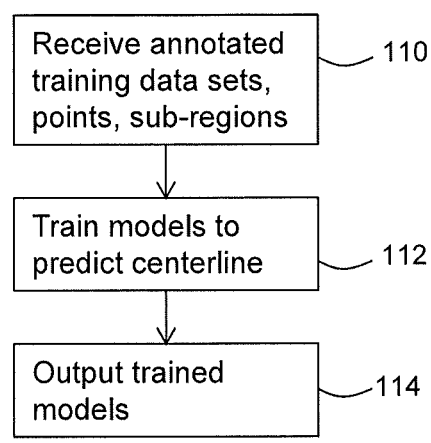
FIG. 7 is a flow chart illustrating in overview a method of training models in accordance with an embodiment.

FIG. 7 is a flow chart illustrating in overview a method of training a combination of a first model (which in the present embodiment is a CNN) and a second model (which in the present embodiment is a recurrent network). At stage 110, the training circuitry 48 receives the plurality of annotated training data sets. The training circuitry 48 receives a plurality of sub-regions centered around points on the tubular structure. At stage 112, the training circuitry 48 trains the combination of the CNN and the recurrent network to predict values for parameters at points on the tubular structure based on parameter values at preceding points on the tubular structure. The training of the models comprises backpropagation. A loss function is used that compares a predicted centerline position to a ground truth centerline position. A gradient of the loss function is computed with respect to the model parameters. In some embodiments, the comparison may be non-linear. A non-linear comparison may be more effective given the non-linear nature of torsion and curvature. At stage 114, the training circuitry 48 outputs the trained first model and trained second model. In other embodiments, the trained first model trained second model may be stored in any suitable memory. The first trained model and second trained model may be implemented in hardware, for example using at least one ASIC or FPGA.

In the embodiment described above, the first and second model are trained concurrently. In further embodiments, a single trained model may provide the functionality of both the first trained model and the second trained model. In other embodiments, the first model and second model may be trained separately.

In some embodiments, a model is trained on a particular type of tubular structure (for example, vessels) and a domain adaptation method is used to adapt the model for use on another type of tubular structure (for example, airways).

In some embodiments, the first model and/or second model comprises a self-learning model. The self-learning model continues to learn while it is in use. The self-learning model may continue to learn as is applied to additional tubular structures. The self-learning model may be automatically refined over time. The self-learning model may update its internal algorithm based on its outputs.

In the embodiments described above with reference to FIGS. 4, 6 and 7, a CNN and an LSTM are used to perform tracking and optionally segmentation. In other embodiments, any trained model or models may be used.

In some embodiments, the first trained model is a machine learning model that outputs a predetermined set of features. For example, the machine learning model may comprise a support-vector machine (SVM). The machine learning model may be configured to receive data relating to a sub-region $\Omega$ and to output a set of computed features. The computed features may include, for example, Gabor features, Hessians, wavelet features, intensity features, gradient features, texture features, or any suitable features. The computed features may be features which are associated with an extent of the vessel within the sub-region, for example features that are indicative of an extent of contrasted blood within the vessel lumen. One or more of the features may be computed for the sub-region as a whole. One or more of the features may be computed for each of a plurality of parts of the sub-region. One or more of the features may be computed for each of a plurality of points (for example, voxels) within the sub-region.

In further embodiments, the first trained model comprises a CNN that is not fully convolutional. Features are reduced to a more limited latent space that is input to the second model (for example, LSTM). In some embodiments, a multi-layer perceptron (MLP) layer or auto-encoder may be used to reduce the features.

Certain embodiments provide an iterative, 3D, recurrent deep learning approach to tubular tree structure tracking, in which the evolution is parameterized using torsion and curvature and include features from a 3D convolution offset between the current and predicted step. The recurrent network may be an LSTM. The regressed parameters may include at least one of: torsion, curvature, step size, vessel radius, number of branch points or structure terminus.

The center of the 3D region from which features are computed using a CNN may be computed as an offset to the next estimated location using the parameters of the previous step and/or including the cuboid defined by including both the current and predicted location. The center may be the halfway point to the estimated location of the next step.

The sampling of the data may be dynamically scaled to a consistent, pre-determined value according to that used for training using the radius estimates from the initial steps (a means of scale invariance). The training data may be scaled to several pixel resolutions (causing scale invariance).

The clinical application of the method may be transformed to another tubular anatomical tree structure using any of a number of domain adaptation techniques.

The tracking iteration may be stopped when one or more branch points are predicted and restarted for each branch.

The 3D convolution may also configured to, or may contain separate/additional layers configured to, perform fully convolutional segmentation of the structure. The fully segmented structure may be determined by the union of parts.

The centerline point position and basis using torsion and curvature may be evolved by performing a Taylor expansion. The centerline point position and basis using torsion and curvature may be evolved assuming small deviations from constant values.

The LSTM may include a narrow window of steps. The LSTM may include the full length of vessel segments (to end or branch).

Certain embodiments provide a method of determining a path of a tubular structure, comprising obtaining volumetric medical imaging data that represents anatomy of a subject including the tubular structure; performing a position-determining procedure that comprises: determining an initial position on said path of the tubular structure, said next point being further along the path than a current point; selecting a sub-region based on said initial position; obtaining values of parameter(s) represents the tubular structure obtained from a region corresponding to the initial position; inputting to a machine learning-derived procedure both data from said selected sub-volume and said parameter values, the machine learning procedure having been trained to determine paths of tubular structures; outputting by the machine learning procedure a position for said next point; updating said initial position to said next point; and repeating the position-determining procedure for updating the initial position thereby to obtain the path of the tubular structure.

Certain embodiments provide a method of determining a path of a tubular structure, comprising obtaining volumetric medical imaging data that represents anatomy of a subject including the tubular structure; performing a position-determining procedure that comprises: determining an initial estimate of a position of a next point on said path of the tubular structure, said next point being further along the path than a current point; selecting a sub-volume based on said initial estimated position of said next point; obtaining values of parameter(s) obtained from the current point and/or preceding point(s) or preceding part(s) of the tubular structure; inputting to a machine learning-derived procedure both data from said selected sub-volume and said parameter values, the machine learning procedure having been trained to determine paths of tubular structures; outputting by the machine learning procedure a position for said next point; and repeating the position-determining procedure for a succession of current and next points thereby to obtain the path of the tubular structure.

Whilst particular circuitries have been described herein, in alternative embodiments functionality of one or more of these circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms. Furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A method of determining a path of a tubular structure using processing circuitry, comprising:
   obtaining volumetric medical imaging data that represents anatomy of a subject including the tubular structure;
   performing position-determining processing comprising:
   obtaining an initial position of a current point on said path of the tubular structure;
   selecting a sub-region based on said initial position;
   obtaining at least one value of at least one parameter representative of the tubular structure;
   inputting to a trained model both data from said selected sub-region and said at least one parameter value, the trained model having been trained to determine paths of tubular structures;
   outputting by the trained model a position for a next point on said path of the tubular structure; and
   updating said initial position to said next point; and
   repeating the position-determining procedure for updating the initial position thereby to obtain the path of the tubular structure.

2. A method according to claim 1, wherein the at least one value for the at least one parameter is representative of a three-dimensional curvature of the path of the tubular structure.

3. A method according to claim 1, wherein the at least one parameter comprises curvature and/or torsion.

4. A method according to claim 1, wherein the at least one value for the at least one parameter is obtained from the current point and/or at least one preceding point on the tubular structure.

5. A method according to claim 1, wherein the position-determining procedure is further configured to output at least one updated value for the at least one parameter.

6. A method according to claim 1, wherein the selecting of the sub-region is based on a determination of an estimated position for the next point.

7. A method according to claim 6, wherein the selected sub-region has a center that is between the respective current point and an estimated position of the respective next point.

8. A method according to claim 1, wherein the trained model is configured to determine presence of a branch point where the tubular structure splits into a plurality of branches; and
   if a branch point is present, the method comprises performing a new succession of position-determining procedures for each of the plurality of branches thereby to determine the paths of each of the plurality of branches.

9. A method according to claim 1, wherein the data from said selected sub-region comprises a convolution.

10. A method according to claim 1, wherein the method further comprises determining the data from said selected sub-region using a further trained model.

11. A method according to claim 10, wherein the further trained model is further configured to perform a segmentation of at least part of the tubular structure.

12. A method according to claim 1, wherein the trained model comprises at least one of a convolutional neural network (CNN), a recurrent network, a long short-term memory (LSTM).

13. A method according to claim 1, wherein the at least one parameter comprises step size.

14. A method according to claim 1, wherein the tubular structure comprises at least one of a blood vessel, an airway.

15. A method according to claim 1, wherein the trained model comprises a self-learning model.

16. An apparatus comprising processing circuitry configured to perform a method for determining a path of a tubular structure, the method comprising:
 obtaining volumetric medical imaging data that represents anatomy of a subject including the tubular structure;
 performing a position-determining procedure that comprises:
 obtaining an initial position of a current point on said path of the tubular structure;
 selecting a sub-region based on said initial position;
 obtaining at least one value of at least one parameter representative of the tubular structure;
 inputting to a trained model both data from said selected sub-region and said at least one parameter value, the trained model having been trained to determine paths of tubular structures;
 outputting by the trained model a position for a next point on said path of the tubular structure; and
 updating said initial position to said next point; and
 repeating the position-determining procedure for updating the initial position thereby to obtain the path of the tubular structure.

17. A method for training a model to determine paths of tubular structures using processing circuitry, the method comprising:
 obtaining a plurality of training sets of volumetric medical imaging data, each representing anatomy of a respective subject including a respective tubular structure;
 obtaining a respective ground truth track for each of the training sets of volumetric medical imaging data;
 for each of the training sets of volumetric medical imaging data, obtaining data for a plurality of sub-regions along the respective tubular structure; and
 training the model to determining paths of tubular structures using data from sub-regions and values for at least one parameter representative of the tubular structure.

18. A method according to claim 17, further comprising scaling at least some of the training sets of volumetric medical imaging data to a standard vessel size and/or to multiple vessel sizes.

19. A method according to claim 17, further comprising transforming at least some of the training sets of volumetric medical imaging data using domain adaptation techniques.

20. An apparatus comprising processing circuitry configured to perform a method for training a model to determine paths of tubular structures, the method comprising:
 obtaining a plurality of training sets of volumetric medical imaging data, each representing anatomy of a respective subject including a respective tubular structure;
 obtaining a respective ground truth track for each of the training sets of volumetric medical imaging data;
 for each of the training sets of volumetric medical imaging data, obtaining data for a plurality of sub-regions along the respective tubular structure; and
 training the model to determining paths of tubular structures using data from sub-regions and values for at least one parameter representative of the tubular structure.

* * * * *